US00PP08533P

United States Patent [19]

Carmel

[11] Patent Number: Plant 8,533

[45] Date of Patent: Jan. 11, 1994

[54] HYBRID TEA ROSE PLANT NAMED 'ALVARO'

[75] Inventor: Carmi Carmel, Moshav Ha'Yogev, Israel

[73] Assignee: Yoval Products Co., Ltd., Moshav Ha'Yogev, Israel

[21] Appl. No.: 710,037

[22] Filed: Jun. 4, 1991

[30] Foreign Application Priority Data

Jun. 5, 1990 [IL] Israel ..... 1585/90

[51] Int. Cl.[5] ..... A01H 5/00

[52] U.S. Cl. ..... Plt./18

[58] Field of Search ..... Plt. 18, 19

*Primary Examiner*—Howard J. Locker

*Attorney, Agent, or Firm*—Pollock, Vande Sande & Priddy

[57] ABSTRACT

A new and distinct cultivar of hybrid tea rose plant is disclosed which exhibits good resistance to powdery mildew. Said cultivar is characterized by non-fragrant flowers, very high crop production, good self-rooting, and high stem break forth.

1 Drawing Sheet

SUMMARY OF THE INVENTION

The present invention is concerned with a new variety of hybrid tea rose discovered by me and being a mutation of the variety Meikola.

BACKGROUND OF THE INVENTION

The mutation was first discovered on a plant of the variety Meikola (U.S. Plant Pat. No. 5,607) as a single branch with a flower distinctly different from the flowers on the other branches. The Meikola plant on which the branch was found was grown in a cultivar area, in the Sierra of Quito, Ecuador, with average night temperature of 5°-14° C., and day temperature of 9°-23° C. From this plant the branch was taken, and cut into cuttings that were brought to Israel.

The cuttings were self-rooted in a greenhouse, in Moshav Ha'Yogev, Israel. From the resulting plants, further plants were vegatatively propagated, also by self-rooting.

Asexual reproduction of this new cultivar as performed at Moshav Ha'Yogev, Israel, shows that the foregoing characteristics and distinctions came true to form and are established and transmistted through succeeding propagations.

The resulting plants were found to be stable in their botanical characteristics as described below and shown in the attached Figure.

The following is a description of the characteristics of my new rose cultivar which distinguishes it from cultivars of which I am aware, especially from Meikola:

1. Distinct larger number of petals.
2. Distinct differences of color, a much darker pink.

BRIEF DESCRIPTION OF THE PHOTOGRAPH

The photograph shows typical specimens of the vegetative growth and flowers of the cultivar of the present invention including a leaf, a flower bud, a flower bud at picking stage, various parts of the stem, leaflets, and flowers at various stages of opening, including with the petals removed, depicted in color as nearly true as it is resonably possible to make the same in a color illustration of this character.

DETAILED DESCRIPTION OF THE INVENTION

The following is a detailed description of new rose cultivar with color in terminology in accordance with The Royal Horticultural Society of London (R.H.S.), England Colour Chart, except where ordinary dictionary significance of color is indicated.

The plant originated as a mutation of Meikola.

The following description of Alvaro is based on observations made in Moshav Ha'Yogev, Israel, in a green-house, and in the Sierra of Quinto, Ecuador, where both varieties (Meikola and Alvaro) were grown in the same green-house, under the same roof and conditions. Both varieties were planted at the same time, from self-rootings, given the same fertilizers, same temperature and ambient conditions, same light, same amount of water irrigation, and same pruning methods.

Plant:

*Growth habit.*—Upright.

Older stem:

*Color.*—Corky and brownish (typical for hybrid tea varieties).

*Short prickles (up to* 1 mm *in length).*—Many.

*Long prickles (up to* 8-10 mm *in length).*—Few. Base part: Shape: Elliptical. Length: About 10 mm. Width: About 2-4 mm. Shape of upper side: Straight. Shape of lower side: Concave. Color: Yellowish brownish RHS 165-C with a brown RHS 166-B point.

Young shoot:

*Color, at lower side, of leaves not yet unfolded.*—Reddish brown RHS 166-A.

*Color of leaves while unfolding changes.*—Green.

*Color, at upper side, of fully expanded leaves.*—Green RHS 144-A.

Leaf:

*Size.*—Length: 110-155 mm. Width: 95-140 mm.

*Color.*—At upper side: Medium green RHS ca. 147-A. At lower side: Grayish green RHS 138-B.

*Glossiness of upper side.*—Weak.

*Description.*—With mainly 5 leaflets; sometimes at the base of the leaf one or two additional small leaflets. Margin of leaflet-serrats. No prickles at lower side of leaf.

Leaflet:

*Cross section.*—Slightly convex.

*Undulation of margin.*—Very weak to weak.

Terminal leaflet:

*Length of blade.*—60–90 mm.

*Maximum width.*—37–55 mm.

*Length of petiole.*—10–18 mm.

*Shape of base.*—Obtuse.

Flowering shoot:

*Number of Flowers.*—One flower per stem in ca. 90% *of the stems; two flowers in* 1% *of the stems; in normal practice, one flower, the second and third flowers are pinched away.—Few.*

*Color.*—Dull green RHS 147-B.

*Short prickles* (*up to* 5 mm *in length*).—Many. Color: Greenish.

*Long prickles* (*over* 5 mm in length).—Few. Color: Greenish. Length of base: 5 mm. Shape of upper side: Somewhat convex.

Flowering habit: Continuous.

Flower pedicel:

*Hair or prickles.*—Many. Color: Whitish. Length (up to 1 mm long): Short.

*Color.*—green RHS 147-B.

*Length, at the stage of loosening of the first petal, between the seed vessel and the upper-most leaf-*.—10–11 cm.

*Diameter in the middle third.*4 mm.

Flower bud:

*Stage 1: color of petals just showing.*—Color: pinkish-red RHS 44-D. Shape in longitudinal direction: Ovoid. Length, including sepals and seed vessel: 30 mm. Maximum diameter: 16 mm.

*Stage 2: first petal begins to loosen* (*picking stage*)-.—Length, excluding seed vessel: 35–38 mm. Maximum diameter: 20–22 mm.

Flower:

*Type.*—Double.

*Number of petals.*—50–70.

*Diameter.*—ca. 100 mm.

*View from above.*—Rounded.

*Side view of upper part.*—Flattened convex.

*Side view of lower part.*—Flat.

*Fragance.*—None.

*Opening flower.*—Petal color: Upper side: Pink RHS 49-A. Lower side: Light pink RHS 49-C. With the progress of the petals' unfolding, the upper side somewhat darkness to Bluer pink.

Sepal:

*Length.*—32–37 mm.

*Extension.*—Weak.

*Color.*—Upper side: Green RHS 144-A.

Petal:

*Typical outer petal of fully opened flower* (*disregarding outermost petals which sometimes do not develop well*).—Length: 45–50 mm. Width: 45–55 mm. Shape: Rounded. Color of middle zone of inner side: RHS 49-A to RHS 52-D pink. Color of marginal zone of inner side: RHS 49-A to RHS 52-D pink. Basel spot of inner side: Present. Size: Large. Color: Light yellow RHS 2-D. Color of middle zone of outer side: Pink RHS 49-A to RHS 52-D. Basel spot of outer side: Present. Size: Large to very Large. Color: Light yellow RHS 4-D.

Reflex margin:

*In inner petals.*—Medium.

*In outer petals.*—Strong. With these reflex margins, the inner and outer petals are thus shaped into a into a rhomboid shape, with a shapr distal point, while the petal base remains straightened out

*Undulation of margin.*—Weak.

Stamen:

*Predominant color of filament.*—Yellowish.

Style:

*Length.*—Long.

*Predominant color.*—Purple.

*Hairiness of upper half.*—Absent.

Stigma:

*Position as compared with anthers.*—Same level.

Pollen:

*Color.*—Yellowish.

*Amount.*—Average for hybrid tea roses.

Seed Vessel:

*Size.*—Small to medium.

*Shape of longitudinal section.*—Pitcher shaped.

*Color at approximately six months from flowering.*—Light brown RHS 164-B with darker brown spots at lower side RHS 165-A.

Seed:

*Color.*—Mainly Yellowish white RHS 161-B.

The time of beginning of flowering is early.

The average number of petals per flower: 50–70 and sometimes, depending on the season, up to 90.

The number of side shoots per flowering branch is 5–6.

The annual production is 150–160 flowers per square meter.

The flowering stem is 70–80 cm long with an average of 13 leaves.

The vase life is up to 15 days, under condition of room temperature.

The average number of water shoots, in first year after planting, is 4–5.

The plant's height in 8 months after planting is about 160 cm.

The time from planting to commercial flower production is 5–6 months.

The variety exhibits good resistance to Rose Powdery Mildew.

The variety exhibits high stem break forth with an average of 4–5 water shoots in the first year after planting, 5–6 side shoots per flowering branch, 160 cm plant height 8 months after planting, 5–6 months from planting to commercial flower production, and 70–80 cm flowering stems with an average of 13 leaves. The variety also exhibits very high crop with an annual production of 150–160 flowers per square meter with 6 plants per square meter. Further, the variety exhibits good self rooting.

Under condition of room temperature, flower opening proceeds slowly.

The variety exhibits very good grafting compatibility on *Rosa indica L.* The variety should be grown under glass.

Comparison of Production Characteristics Between the New Variety "Alvaro" and Variety "Meikola"

Observations made in the Sierra of Quito, Ecuador and at Moshav Ha'Yogev, Israel as compared with U.S. Plant Pat. No. 5,607:

| | ALVARO | MEIKOLA |
|---|---|---|
| Flower - average number of petals | 50–70 | 25 |
| Color of petal | RHS 40-A to 52-D dark pink | RHS 49-D French pink |

I claim:

1. A new and distinct variety of hybrid tea rose plant, named Alvaro, substantially as herein shown and described, and characterized by the following combination of distinguishing traits: vigorous growth, a large flower bud, a large number of petals, non-fragrant flowers, a large yellow spot at the petal base, early and prolific flower production, and excellent propagating features.

* * * * *

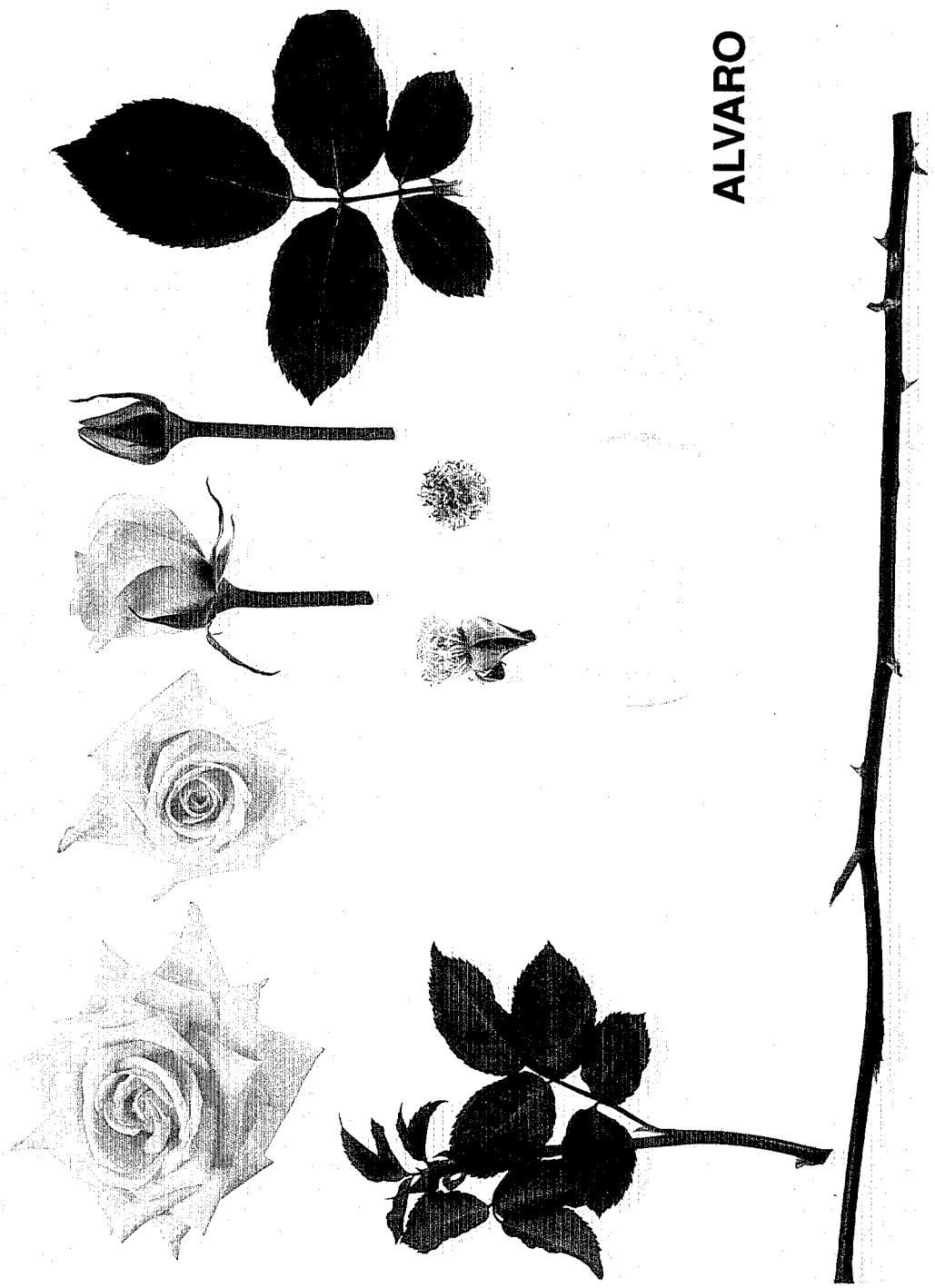
ALVARO